(12) United States Patent
Pollock et al.

(10) Patent No.: US 8,912,709 B2
(45) Date of Patent: Dec. 16, 2014

(54) FLEXI-PCB MOUNTING OF ULTRASONIC TRANSDUCERS FOR ENHANCED DERMAL AND TRANSDERMAL APPLICATIONS

(75) Inventors: Neil Pollock, Royston (GB); Paul Mark Galluzzo, Cambridgeshire (GB); Grant Corthorn, Cambridgeshire (GB)

(73) Assignee: Sonovia Holdings LLC, Topeka, KS (US)

( * ) Notice: Subject to any disclaimer, the term of this patent is extended or adjusted under 35 U.S.C. 154(b) by 545 days.

(21) Appl. No.: 13/394,602

(22) PCT Filed: Aug. 19, 2010

(86) PCT No.: PCT/GB2010/001569
§ 371 (c)(1),
(2), (4) Date: Jul. 10, 2012

(87) PCT Pub. No.: WO2011/027093
PCT Pub. Date: Mar. 10, 2011

(65) Prior Publication Data
US 2012/0277639 A1 Nov. 1, 2012

(30) Foreign Application Priority Data
Sep. 7, 2009 (GB) .................................. 0915593.8

(51) Int. Cl.
*A61B 8/14* (2006.01)
*H01L 41/09* (2006.01)
*G10K 11/00* (2006.01)
*B06B 1/06* (2006.01)

(52) U.S. Cl.
CPC ............ *B06B 1/0629* (2013.01); *G10K 11/004* (2013.01)

USPC .......................................... 310/334; 600/457

(58) Field of Classification Search
CPC ...................................................... H04R 17/006
USPC ......................................... 310/334; 600/459
See application file for complete search history.

(56) References Cited

U.S. PATENT DOCUMENTS 3,847,016 A * 11/1974 Ziedonis ....................... 600/453
3,927,662 A   12/1975 Ziedonis
(Continued)

FOREIGN PATENT DOCUMENTS

| WO | WO 02/052544 | 7/2002 |
| WO | WO 2008/137030 | 11/2008 |
| WO | WO 2010/054014 | 5/2010 |

OTHER PUBLICATIONS

Combined Search and Examination Report from the Intellectual Property Office of the United Kingdom dated Jan. 6, 2010 received for priority Great Britain Patent Application 0915593.8 (7 pgs).

(Continued)

*Primary Examiner* — Thomas Dougherty
(74) *Attorney, Agent, or Firm* — Stinson Leonard Street LLP

(57) ABSTRACT

An ultrasound transducer patch (100) comprises an array of ultrasound transducers (20) mounted to a flexi-PCB (10) containing multiple tracks (12). Each transducer (20), or a subgroup of the transducers is electrically connected to first and second of the multiple tracks. The flexi-PCB (10) is configured, such as by virtue of cut-out portions (114, 414) or by inherent elasticity, to be bendable a out non-parallel axes. The enables the patch (100) to readily conform to a complex 3D surface such as a portion of a patient's face to ensure efficient transmission of ultrasound energy to a desired area of treatment.

35 Claims, 5 Drawing Sheets

(56) References Cited

U.S. PATENT DOCUMENTS

| | | | |
|---|---|---|---|
| 5,871,446 A * | 2/1999 | Wilk | 600/407 |
| 6,025,670 A * | 2/2000 | Corl et al. | 310/369 |
| 7,497,828 B1 * | 3/2009 | Wilk et al. | 600/443 |
| 8,235,907 B2 * | 8/2012 | Wilk et al. | 600/447 |
| 2007/0013264 A1 * | 1/2007 | Wilser et al. | 310/311 |
| 2007/0167133 A1 * | 7/2007 | Tomlinson et al. | 455/39 |
| 2008/0178677 A1 | 7/2008 | Baumgartner et al. | |
| 2010/0191119 A1 * | 7/2010 | Muthya et al. | 600/453 |
| 2014/0058263 A1 * | 2/2014 | Baym et al. | 600/447 |

OTHER PUBLICATIONS

International Search Report and Opinion dated Dec. 15, 2010 received for priority PCT application PCT/GS2010/001569 (11 pgs).

* cited by examiner

FLEXI-PCB MOUNTING OF ULTRASONIC TRANSDUCERS FOR ENHANCED DERMAL AND TRANSDERMAL APPLICATIONS

FIELD OF THE INVENTION

This invention relates generally to the mounting and wiring of ultrasonic transducers in an array to a patch for the delivery of ultrasound for dermal and transdermal applications. More particularly, the application relates to the mounting and wiring of such a transducer array by use of a flexi-PCB.

BACKGROUND TO THE INVENTION

Traditionally, ultrasound has been applied through hand-held transducer probes/heads in diagnostic and therapeutic scenarios. The 'head' has to be continuously moved for both practical and safety reasons. In diagnostic scanning, dynamic images are displayed on a screen and movement allows the object to be viewed from multiple angles. The time averaged intensities are lower in diagnostic ultrasound but nevertheless constant movement also minimises cumulative ultrasound exposure of a given volume of soft or hard tissue. Therapeutic ultrasound (e.g. physiotherapy) utilises higher (averaged) intensities of ultrasound and is employed purely to provide a physiological response, e.g. muscle repair following a sporting injury.

Constant movement of hand-held devices is important to avoid over and under exposure. Over-exposure can lead to over-heating/thermal damage and also standing waves being created with the potential to cause lysis of cells. Conversely, under-exposure will reduce the amount of ultrasonic energy received by a particular area of the body and therefore cause reduced therapeutic benefit.

Relying on manual movement of the device is unreliable and cannot guarantee even coverage and therefore even exposure. Some areas will not receive the same level of treatment as others and are highly dependent on the abilities of the practitioner to keep the device moving at a constant steady speed potentially over a 20-30 minute period leading to arm/wrist/hand fatigue and uneven treatment of the patient. Electronic movement over an array of transducers will obviate operator error normally associated with uneven/erratic movement of an otherwise hand-held device.

The underlying technology on which this invention is based is thin, flexible patches or bandages containing an array of ultrasound transducers that operate in close contact with complex bodily surfaces such as the face. As with all applications and geometries of applied ultrasound, to perform correctly there needs to be an 'air-free' acoustic path for the ultrasound from transducer surface to skin surface. Air cavities/bubbles etc would severely impede propagation of ultrasound due to their significantly lower acoustic impedance causing reflection and refraction of the propagating wave so lowering the intensity of ultrasound impinging on and propagating through the skin.

Such a flexible ultrasound patch would thus need to conform closely to bodily surfaces and avoid, as much as possible, any buckling of the patch to allow air spaces to come between the patch and the skin. This problem may be overcome somewhat by using free-flowing gels that fill any air-spaces.

Arrays of transducers need to be wired to enable every element in that array to be activated. This wired array also needs to be encapsulated to prevent water (e.g. coupling gel) ingress and general soiling. Encapsulating materials that have some inherent elasticity may allow moulding to doubly curved surfaces, but the associated electrical circuit contained within is most unlikely to allow such complex bending.

Within the ultrasonic patch, each of the transducers require robust electrical interconnection that can withstand frequent and numerous flexing/bending. Failure of the connections could result in a transducer failing to operate and may even cause failure of entire sub-groups of transducers.

Therefore, there needs to be an electrical interconnecting system that can withstand repetitive bending while allowing moulding to complex surfaces.

Materials applied to the surface of the human body or other complex shapes typically employ some degree of tension in many directions to keep the material in contact with that object, e.g. Lycra/Spandex™ clothing. Flexible sheets of material such as paper can easily conform to singly curved shapes, e.g. cylindrical, but have difficulty in conforming to doubly curved shapes, e.g. a sphere.

It is known to mount an array of transducers on a flexible printed circuit board (flexi-PCB). Previous studies (e.g. Arunachalam et al., 2008, 'Performance evaluation of a conformal TMS sensor array' *Int. J. Hyperthermia,* 24(4), 313-325) describe flexible PCB mounted temperature sensors for measuring skin surface temperatures. The study employed multi-layer Kapton® polyimide film which is known to have stable mechanical, physical and thermal properties as well as high tensile strength and folding endurance (285 k cycles) suitable for use when wrapped around the human torso.

However, the Arunachalam et al. study uses a single continuous sheet of flexible PCB. That sheet of flexi-PCB would curve and bend to conform to a cylindrical geometry, but not to a doubly curved surface such as a sphere or a saddle point.

WO 2008137030(A1), entitled 'A flexible conformal ultrasonic imaging transducer and system', discloses a system that is intended for, but not limited to, ultrasonic imaging via send and receive ultrasonic pulses. A conformal flexible transducer array for contact to various parts of the human body is disclosed. However, like the conformal TMS array described in Arunachalam et al, the transducers are mounted on a continuous sheet of Kapton® polyimide flexible printed circuit substrate which would limit the number of bending directions to one, hence only achieving close conformity to a singly curved surface such a cylinder.

U.S. Pat. No. 5,735,282 (A) discloses the mounting of a linear 1D array of ultrasound transducers on multiple flex circuit segments, wherein sub-groups of the transducers in the linear array are respectively mounted on different flex circuits. It is stated that in an array of 128 PZT elements, each on a 0.3 millimeter pitch, it may be advisable to have eight or more individual flex segments. The more flex segments that are used, the greater the ability of the array to flex. However, when multiple layers of flex circuit are folded on top of one another, there can be a disadvantage associated with the increased overall thickness of the assembly and the increased vulnerability to cross-talk. In fact, the linear array must only flex along the azimuth, although because of the way the arrangement is constructed, the individual flex circuits must also simultaneously fold around the back of the array.

SUMMARY OF THE INVENTION

According to the invention, there is provided an ultrasound transducer patch comprising:
an array of ultrasound transducers; and
a flexi-PCB containing multiple tracks;

wherein each of the transducers in the array is mounted on the flexi-PCB, each transducer being electrically connected to first and second of the multiple tracks of the flexi-PCB; and wherein the flexi-PCB is configured so as to be bendable about non-parallel axes.

By providing a flexi-PCB that is configured so as to be bendable about non-parallel axes, the array of transducers mounted thereon is able to conform to a complex 3D surface, such as a portion of a face. Accordingly, the transducers are each able to deliver ultrasound efficiently to the underlying surface.

The flexi-PCB may include cut-out portions to provide the required bendability. The cut-out portions may define multiple fingers, each finger including at least first and second tracks and at least one transducer electrically connected to those tracks. Alternatively, the cut-out portions may define a mesh of lands interconnected by bridges, each land including at least first and second tracks and at least one transducer electrically connected to those tracks.

Alternatively, multiple tracks or islands of flexi-PCB mounted ultrasonic transducers could be held within an elastomeric matrix whereby tension applied to the matrix would increase the spacing between these sub-groups and so allow different radii of curvature across the patch. Such a patch under tension could be a large area cuff around a limb or a simple band around the head.

The transducers may be grouped into sub-groups, with at least first and second respective tracks addressing each sub-group. The sub-groups may be mounted on respective fingers or lands.

With the (sub-groups of) transducers mounted on individual fingers, each having first and second tracks, then these sub-groups could be encapsulated within, for example, a medical grade elastomer to form individual fingers that can move independently of each other allowing doubly-curved surface moulding. Similarly, with the (sub-groups of) transducers mounted on individual lands, the interconnecting bridges allow each track to bend and mould independently of each other for such independent conformance. By virtue of the first and second tracks on each finger or land, all of the transducers on a particular finger or land may be addressed simultaneously. This arrangement reduces the number of tracks needed to address each transducer and simplifies the connections, simultaneously meaning that fewer tracks are needed for each finger or land, thus enhancing the flexibility of the finger or land relative to the remainder of the patch.

The transducers may be clustered in sub-groups, positioned and addressed so as to provide enhanced depth of penetration when driven. The transducers of the type necessary for use in a treatment patch according to the invention must be relatively small and therefore have a limited depth of penetration. It has been determined that by arranging individual transducers in a cluster, the depth of penetration of the cluster is greater than that which can be achieved by such an individual, small transducer.

The ultrasound transducer patch may further comprise an electrical cable for connection to electrical drive means, the cable including leads connected to conductive pads on the flexi-PCB that are electrically connected to the respective tracks. The ultrasound transducer patch may further comprise a connector assembly enclosing the connections between the leads of the cable and the conductive pads of the flexi-PCB.

The cable enables connection to a remote drive means, so the patch itself does not have to include this. This enables the patch to be lightweight and comfortable for the user. The addition of a connector assembly helps to protect the connections between the leads in the cable and the pads and hence the tracks of the flexi-PCB. Moreover, the connector assembly can ensure that the connection is protected by a fluidic seal to prevent shorting of the electrical connections.

According to another aspect of the invention, there is provided an ultrasound treatment system comprising:
an ultrasound transducer patch as described above and including an electrical cable; and
electrical drive means coupled to the patch via the cable.

The system may typically be adapted to be worn on a user's body and allow ambulatory use. In conventional (e.g. physiotherapy) ultrasound devices, the drive means may be a separate unit, and may even be portable, but these have not been designed to be worn by the user. There would be no reason to make such an adaptation, because the use of such a device is limited to trained personnel, not by the user themselves. In contrast, with the inventive system, the user (i.e. the person on whom the ultrasound treatment is being applied) is able to remain mobile which using the system.

It is envisaged that the drive means, with appropriate power source, such as a battery, could be incorporated into the patch itself, in which case there would be no need for a cable to couple the drive means to the patch.

BRIEF DESCRIPTION OF THE DRAWINGS

The invention will be described, by way of example, with reference to the accompanying drawings, in which:

FIG. 2b is a bottom perspective view of the ultrasound treatment patch of FIG. 2a;

DETAILED DESCRIPTION

The invention is for a flat, flexible PCB 10 (flexi-PCB) which allows the mounting and electrical drive of one or more dual-frequency ultrasonic transducers 20. The combination of the transducers 20 and the flexi-PCB 10 then forms a flexible patch 100 which is capable of applying ultrasonic energy over an area in a flexible format which can form to allow effective contact on a 3D surface.

Figure 1A:
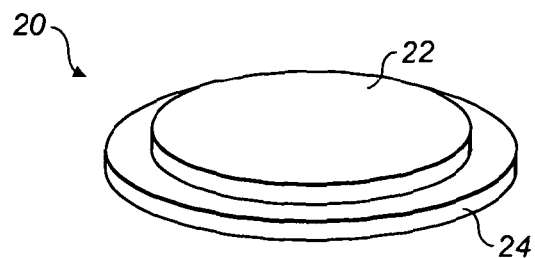
FIG. 1a is a schematic perspective view of a dual-frequency ultrasound transducer.
Figure 1B:
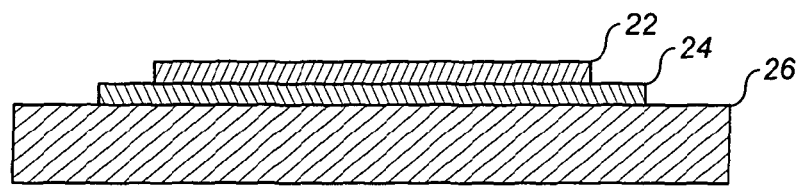
FIG. 1b is a cross-sectional view of the transducer of FIG. 1a, mounted on an acoustic medium.

FIGS. 1a and 1b show a typical structure for a dual-frequency transducer 20, which comprises a piezo-electric, circular plate 22 bonded concentrically to a circular plastic or metal substrate 24. This construction allows the generation of acoustic energy at two different frequencies. The transducer construction used to generate the double frequency is to have a single device (the 'transducer' 20) vibrate in both bending mode (for the low frequency, 50 kHz) and thickness mode (for the high frequency, 3 MHz). The transducer 20 is a "unimorph", in other words a piezo-electric plate 12 bonded to an elastic substrate (also a plate 24). The transducer 20 is able to transmit the above ultrasonic frequencies, under appropriate drive control, into an underlying acoustic medium 26.

Alternative formats for the transducer 20 construction are possible—and these include alternative shapes (eg. a square piezo-electric plate 22 and square elastic substrate 24) and alternative structures (e.g. a "bimorph" structure which would consist of two piezo-electric plates 22 sandwiching a thin, conductive layer, with no elastic substrate required). Possible advantages of a square shaped transducer 20 would be to maximise the area of the skin directly covered by an array of closely packed transducers 20. Ad vantages of a "bimorph" structure would be the increased vibrational amplitude compared to a "unimorph" transducer 20 for the same level of electrical drive.

Figure 2A:
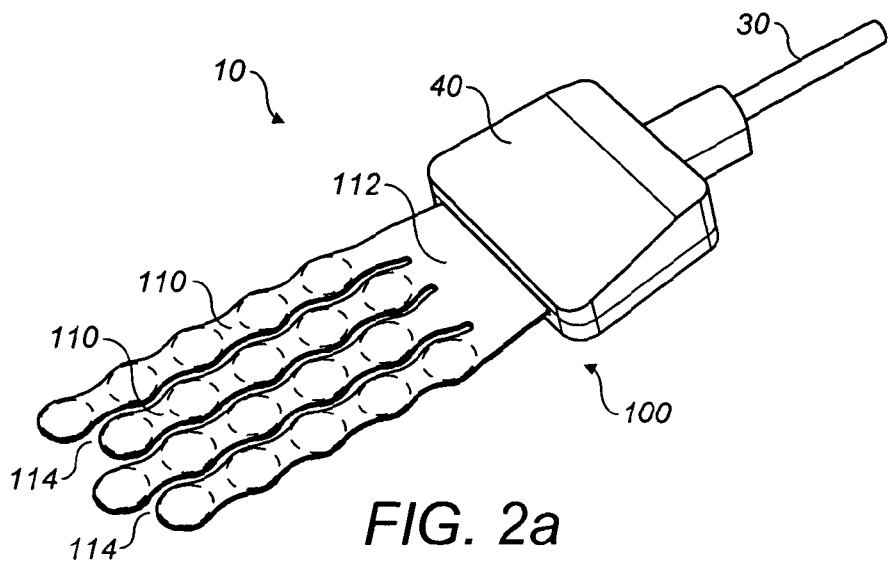
FIG. 2a is a top perspective view of an ultrasound treatment patch according to one embodiment.
Figure 2B:
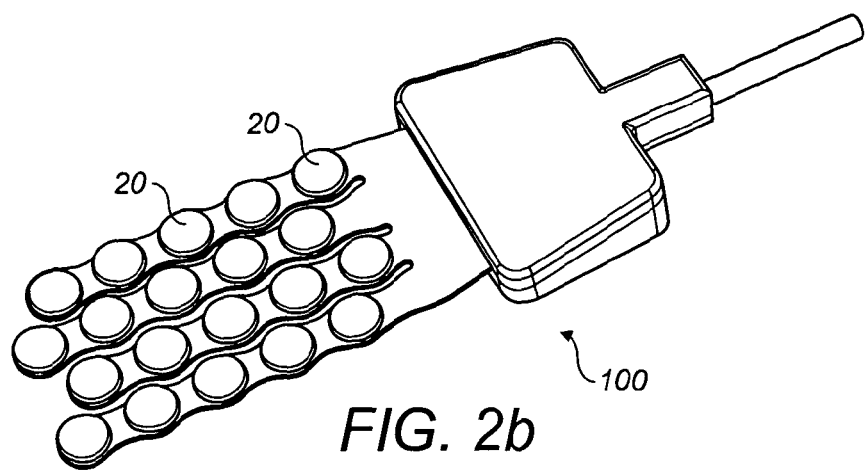

An exemplary patch 100 is shown in FIGS. 2a and 2b and generally comprises a flexi-PCB 10 on which is mounted a plurality of transducers 20. The transducers are each electrically connected to respective first and second tracks 12 within the flexi-PCB, as described more fully below. External electrical drive to the patch 100 is provided via an electrical cable 30 (the 'umbilical') which has electrical connections soldered directly onto conductive pads on the flexi-PCB 10. A simple connector assembly 40 is used to protect these soldered connections and to provide mechanical robustness to the soldered joint (and a fluidic seal to prevent shorting of the electrical connections).

The patch 100 may be held in contact with the target surface via an elastic or non-elastic bandage, which applies a pressure to the patch to ensure that all transducers 20 contact the target surface. An acoustic gel may be manually applied to the patch 100 or skin in order to provide an effective acoustic coupling.

The acoustic medium 26 may be the skin and underlying flesh of a patient or may be an intermediate medium, such as an acoustic gel or gel pad, to improve the transmission of the ultrasound energy to the desired area. This pad could be applied directly to individual or groups of transducers 20 and could have double-sided adhesive layers. This would allow the patch 100 to be attached directly to the skin surface with no need for bandages. This would make it easier to apply the patch to areas of the body which are cannot support the use of a bandage (e.g. the face or head)

Figure 3:
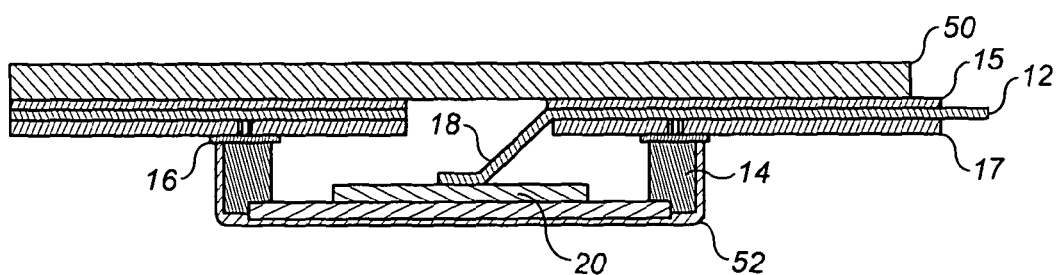
FIG. 3 is a cross-sectional view of an arrangement for mounting a transducer to a flexi-PCB.

With reference to FIG. 3, the flexi-PCB 10 is manufactured using industry standard methods—with multiple, bonded layers to provide the electrical tracks 12 and electrical insulation required for the patch construction. The electrical tracks 12 comprise the means to drive the transducers 20. Layers 15, 17 above and below these electrical tracks 12 contain a conductive grid pattern which can be driven electrically in order to provide EMC shielding—to reduce the EMC emissions from the patch 100. The transducers 20 are electrically and mechanically mounted to specific locations on the flexi-PCB 10. Where required, groups of transducers can be electrically connected in parallel using the conductive tracks 12 in the flexi-PCB 10—the tracks are capable of carrying the maximum current required to drive the transducers.

Each transducer 20 is mounted to a lower, active surface of the flexi-PCB 10 by way of a conductive mounting ring 14 that is electrically connected at its upper end to a conductive pad 16 that is in turn electrically connected to a first track. The lower end of the mounting ring 14 is secured to the elastic substrate 24 using an electrically conductive adhesive. The mounting ring 14 is bonded to the conductive pad 16 using a solder and/or electrically conductive adhesive. Electrical connection of the transducer 20 to a second track is made via a conductive flexible tab 18 that makes an electrically connection to the piezo-electric plate 22. The flexible tab 18 is bonded to the upper surface of the piezo-electric plate 22 using a solder and/or electrically conductive adhesive. The transducer surface is slightly proud of the mounting ring 14 in order to ensure that the transducer 20 contacts the acoustic medium 26 effectively.

A flexible layer 50 may also be attached to the upper surface of the flexi-PCB 10 in order to seal and cover any exposed electrical connections to the transducers 20. A conformal coating layer 52 is applied to the active surface of the transducer (the substrate 24 and mounting ring 14) in order to provide adequate electrical insulation.

The shape of the flexi-PCB 10 allows a degree of conformance to a 3D surface. The exemplary patch 100 of FIG. 2 uses a number of flexible 'fingers' 110 extending distally from a common portion 112, each finger 110 carrying five transducers 20 (the individual transducers 20 of a finger 110 may be grouped electrically and driven in parallel, each being connected to common first and second tracks 12). The fingers 110 are defined by interceding cut-out portions 114.

Figure 4A:
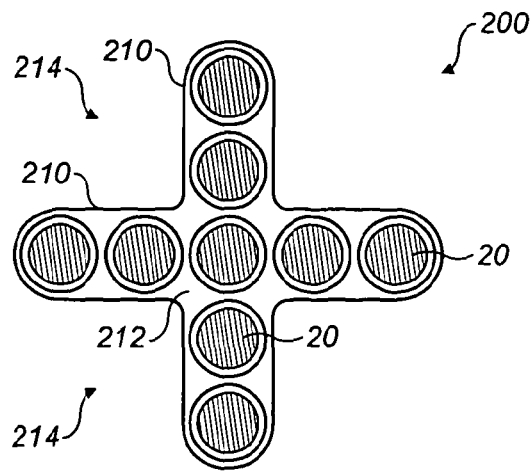
FIGS. 4a-c show alternative ultrasound treatment patches.
Figure 4B:
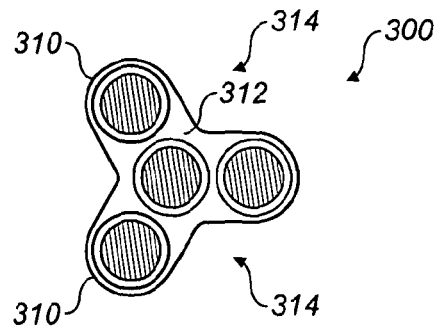
Figure 4C:
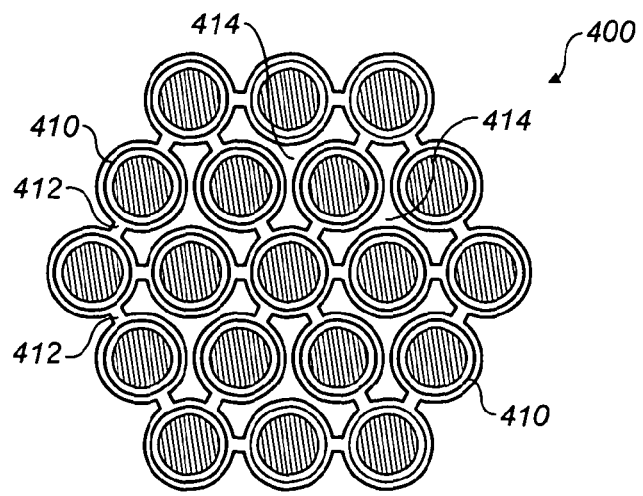

Alternative examples are shown in FIGS. 4a-c. For example, FIG. 4a shows a cross-shaped patch 200 having four fingers 210 extending from a common central portion 212 and defined by cut-out portions 214. FIG. 4b shows a patch 300 having three fingers 310 extending from a common central portion 312 and defined by cut-out portions 314. FIG. 4c shows an alternative patch 400 comprising a mesh of lands 410 interconnected by bridges 412, each land 410 including at least first and second tracks and at least one transducer 20 electrically connected to those tracks. The lands 410 and bridges 412 are defined by cut-out portions 414. In this arrangement, each land 410 can tilt relative to its neighbours by flexing of the connecting bridges 412. Accordingly, the transducer 20 or sub-group of transducers on each land can tilt relative to the other transducers.

Figure 6:
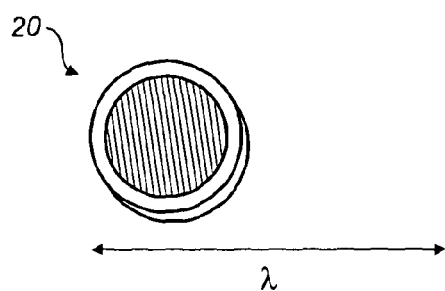
FIG. 6 is an illustration of a small transducer for use in a patch according to the invention, showing a typical size compared to the wavelength of the low frequency ultrasound component.
Figure 7:
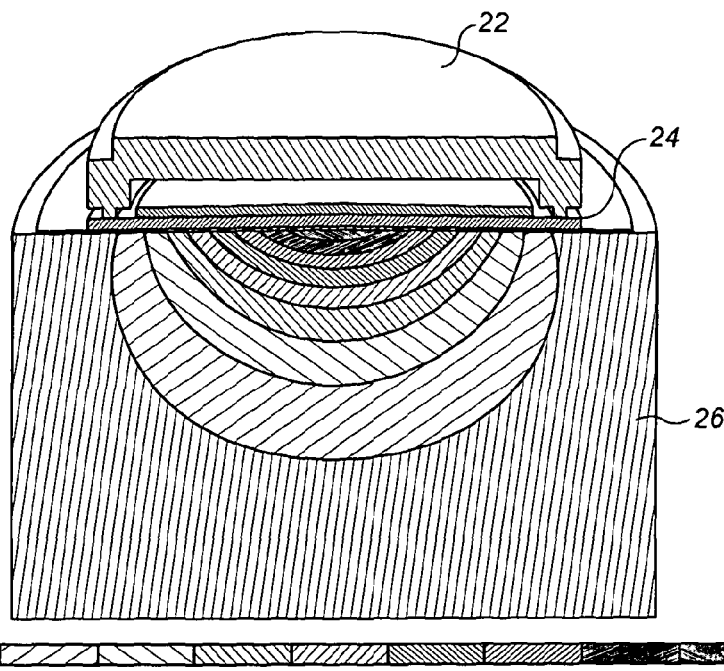
FIG. 7 is a plot showing depth of propagation of the transducer of FIG. 6.

Due to the array of multiple transducer elements needed to achieve a thin, flexible patch 100, the individual transducers 20 are small compared to those incorporated into conventional (e.g. physiotherapy) devices. This has the implication that, at low frequencies, each individual transducer 20 is small compared to the wavelength of the low frequency ultrasound component (see FIG. 6) and consequently limits its depth of propagation due to the divergent beam profile as shown in FIG. 7.

In general, the depth of penetration can be increased by:
1. Increasing the diameter of each transducer 20 in the array;
2. Decreasing the spacing between each transducer 20; and
3. Increasing the intensity (e.g. in $W/cm^2$) of ultrasound emitted from each transducer 20.

Figure 8:
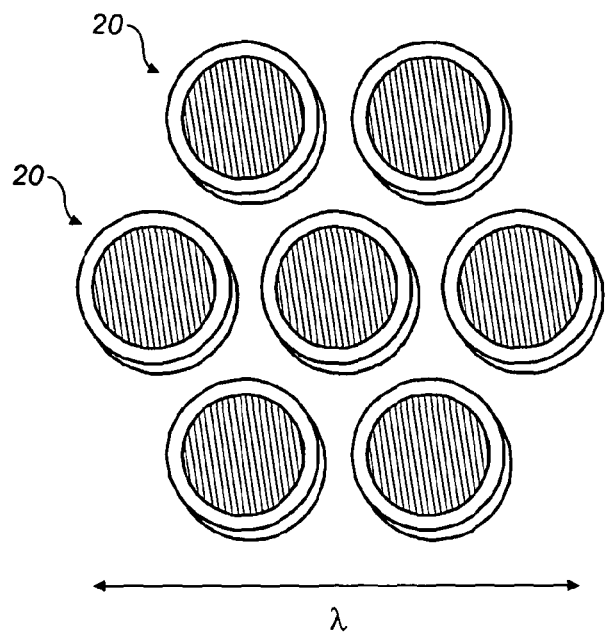
FIG. 8 is an illustration of a cluster of transducers of the type shown in FIG. 7, showing a typical size compared to the wavelength of the low frequency ultrasound component.

However, recent modelling work shows how 'clustering' of individual transducers 20 can provide an additive 'field' effect which greatly extends the depth of penetration. A typical cluster arrangement is shown in FIG. 8, with results of a typical enhanced depth of penetration model being shown in FIG. 9. This clustering of transducers, and associated enhanced depth of penetration opens up the opportunity to provide regenerative therapy from a thin patch 100 to target deeper e.g. musculoskeletal locations as well as more superficial dermal layers. Such 'clusters' of transducers 20 can thus be mounted onto individual flexi-PCB 'islands' and then incorporated into patches, cuffs and other forms of therapeutic covering. For example, each finger 110, 210, 310 or land 410 of the above exemplary patches 100, 200, 300, 400 could have mounted thereon a cluster of transducers 20 positioned and addressed so as to provide enhanced depth of penetration when driven.

Figure 9:
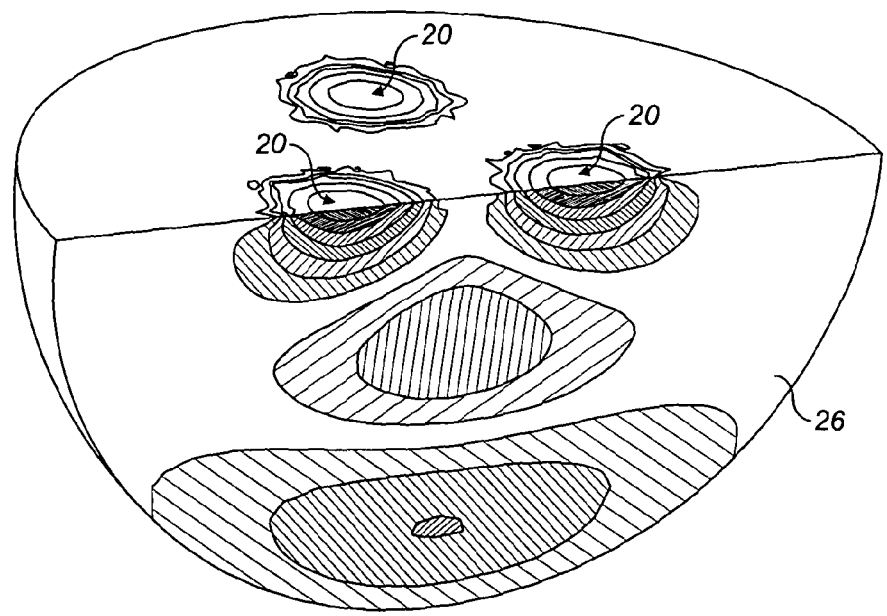
FIG. 9 is a plot showing enhanced depth of propagation of a transducer cluster.

The numerical modelling example shown in FIG. 9 demonstrates how effective depth can be enhanced with such clustered groups of transducers 20. It is envisaged that groups of e.g. 4-7 transducers 20, each mounted on conformable portions of flexi-PCB 10, will provide improved depth of penetration as the combined width of these group sizes near the wavelength of ultrasound in soft tissue (FIG. 8).

The flexi-PCB 10 incorporates specific features such as:
Integrated, conductive tracks 12 to allow the driving of the transducers 20. The tracks 12 would be capable of supplying the power required to operate the transducers whilst still allowing the patch 100 to flex. The tracks 12 can be laid out such that arrays (i.e. sub-groups) of transducers 20 can be driven in parallel—so reducing the total number of input drive channels.
Simple method of electrical connection from the flat flexi-PCB format to a drive cable 30 (or 'umbilical') via soldered connections. The number of electrical connections would be minimised if groups of transducers 20 are driven in parallel.
Electrically driven EMC shielding layers 15, 17 (to minimise the emissions of EMC from the patch 100)
Low cost electrical connections between the flexi-PCB 10 and the transducers 20. These connections could be via pads 16 or tracks on the outer layer(s) of the flexi-PCB 10.
Specific shaping (e.g. 'fingers' 110) of the flexi-PCB 10 to allow patch conformity to 3D structures.
Potential use of double-sided low tack adhesive gel pads to attach the ultrasonic transducers 20 to skin—either a large pad for a group of transducers or individual gel pads for individual transducers.
The flexi-format would also simplify the inclusion of additional conductive tracks 12 and additional functionality in the patch 100 such as
sensors (e.g. thermistors for thermal control)
buzzers
LEDs
micro-switches
resistive heating tracks
solid-state cooling elements
Conformal die-electric coating of the transducer substrates in order to provide electrical insulation.

An alternative transducer mounting method may be used in order to maximise the acoustic penetration of the lower frequency mode. This could be achieved by providing a simple line contact between the rigid mounting ring 14 and the transducer substrate 24 and then using a compliant material (e.g. elastomeric adhesive, silicone rubber) to ensure contact between the mounting ring 14 and the transducer 20.

Instead of the transducer(s) 20 being connected to the flexi-PCB 10 using the mounting methods described above, a wrap-around electrode may be used on the piezo-electric plate 22 thus to electrically connect the transducer 20 to the flexi-PCB 10 via:
soldered wires which are fed through a hole in the flexi-PCB 10; or a miniature flexi-PCB.

Instead of the electrical connection to the piezo-electric plate 22 being made by the flexible tab 18, an alternative method of achieving the electrical connection could be achieved via a soldered or conductive adhesive joint:
using a soldered wire which is fed through a hole in the flexi-PCB 10; or
using a miniature flexi-PCB to connect the transducer 20 and to the flexi-PCB 10 (on the main patch flexi-PCB this connection could be via a soldered or plug connection)

Another alternative mounting arrangement is reverse mounting of the transducers 20 (transducers 20 mounted on the top of the flexi-PCB 10). Main advantage may be the fact that transducers 20 will move away from each other as the patch 100 flexes—so the initial transducer pitch can be minimised. The flexi-PCB 10 can also act as an effective electrical barrier and be easy to clean. Such mounting would be achieved by:
attaching the transducer 20 to the upper surface of the flexi-PCB 10
Possible advantages are that the flexi-PCB layer under the actuator could have a driven EMC shield layer, so EMC protection is maximised.
attaching the piezo disk 22 directly to the flexi-PCB 10.
This would reduce part count and cost. The material stiffness and thickness of the flexi-PCB underneath the piezo disk would have to allow the generation of the low frequency mode.

Further alternatively, the transducer substrate material 24 may be dished, forming a cavity in which the piezo-electric plate 22 can be housed, to reduce the cost of the transducer sub-assembly by eliminating the need for a mounting ring 14.

Further alternatively, the contact surface of the transducer substrate 24 may be shaped in order to minimise the risk of air inclusions if a liquid acoustic coupling gel is used.

Figure 5:
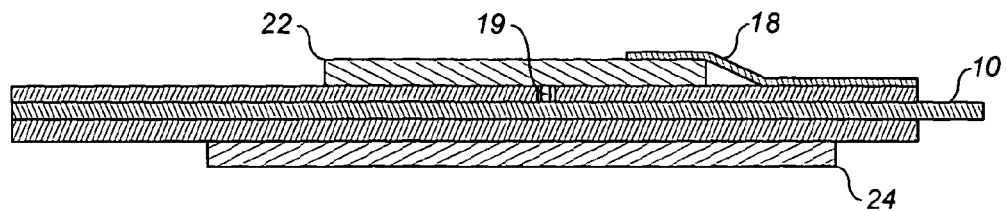
FIG. 5 is a cross-sectional view of an alternative arrangement for mounting a transducer to a flexi-PCB.

Further alternatively, as shown in FIG. 5, the circular piezo-electric plate 22 could be bonded directly to the upper surface of the flexi-PCB 10 and the transducer substrate 24 could be bonded in an aligned location to the bottom surface of the flexi-PCB 10. Advantages would be that it simplifies the electrical connection between the upper surface of the flexi-PCB 10 and the piezo-electric plate 22, such as by means of a flexible tab 18 and a conductive via 19; a raised substrate on the lower surface of the flexi-PCB 10 will help to ensure good acoustic contact with the skin (an advantage over the simple reverse mounted alternative); and surfaces of the patch 100 in contact with the skin will be electrically insulated from the electrical drive system. There may also be manufacturing advantages to assembling the piezo-electric plate 22 directly to the flexi-PCB 10 rather than to the transducer substrate 24.

The flexi-PCB 10 may be plugged directly into a socket connector on a PCB, such that the cable 30 and connector 40 are re-usable and the flexi-PCB 10 (and patch 100) can be easily replaced after one or more uses.

Areas of application for the patch 100 include: cosmetic dermatology, medical dermatology (e.g. wound healing[a]), transdermal drug delivery, physiotherapy and bone healing[b]. No significant modifications would be required as the essential characteristics of the flexible patch 100 would be the same, i.e. to conform to complex surfaces.

[a] Dyson, M and Smalley, D: Effects of ultrasound on wound contraction. In Millner, R and Corket, U (eds): Ultrasound Interactions in Biology and Medicine. Plenum, New York, 1983, p 151.
[b] Li J. K.; Chang W. H. 1; Lin J. C.; Ruaan R. C.; Liu H. C.; Sun J. S., Cytokine release from osteoblasts in response to ultrasound stimulation, Biomaterials, Volume 24, Number 13, June 2003, pp. 2379-2385(7)

In the cases of medical dermatology, transdermal drug delivery, physiotherapy and bone healing, the technology would be equally applicable to all relevant veterinarian applications.

Although the invention has been described by reference to a patch including dual-frequency transducers, it will be appreciated that the mounting concept applies equally to other forms of transducers, such as conventional single-frequency transducers.

The invention claimed is:

1. An ultrasound transducer patch, comprising:
   a flexible printed circuit board; and
   at least one transducer cluster comprising a plurality of transducers mounted to the flexible printed circuit board, wherein each of the transducers is operable to generate ultrasound having a wavelength, and wherein the transducers are arranged such that the transducer cluster has a width of about the wavelength of the ultrasound.

2. The ultrasound transducer patch of claim 1, wherein each of the transducers comprises a single-frequency transducer.

3. The ultrasound transducer patch of claim 1, wherein each of the transducers comprises a dual-frequency transducer.

4. The ultrasound transducer patch of claim 3, wherein each of the transducers has a unimorph structure.

5. The ultrasound transducer patch of claim 3, wherein each of the transducers has a bimorph structure.

6. The ultrasound transducer patch of claim 3, wherein the ultrasound generated by each of the transducers has a low frequency ultrasound component and a high frequency ultrasound component, and wherein the transducer cluster has a width of about the wavelength of the low frequency ultrasound component.

7. The ultrasound transducer patch of claim 6, wherein the low frequency ultrasound component is generated at 50 kHz and the high frequency ultrasound component is generated at 3 MHz.

8. The ultrasound transducer patch of claim 1, further comprising a plurality of transducer clusters each having a width of about the wavelength of the ultrasound.

9. The ultrasound transducer patch of claim 8, wherein each of the transducer clusters includes 4 to 7 transducers.

10. The ultrasound transducer patch of claim 8, wherein the flexible printed circuit board includes a plurality of cut-out portions so as to be bendable about non-parallel axes.

11. The ultrasound transducer patch of claim 10, wherein the cut-out portions define multiple fingers, wherein each of the fingers includes first and second conductive tracks and at least one transducer cluster electrically connected to the conductive tracks, and wherein the conductive tracks are capable of supplying power to the transducers in the transducer cluster.

12. The ultrasound transducer patch of claim 10, wherein the cut-out portions define a mesh of lands interconnected by bridges, wherein each of the lands includes first and second conductive tracks and at least one transducer cluster electrically connected to the conductive tracks, and wherein the conductive tracks are capable of supplying power to the transducers in the transducer cluster.

13. An ultrasound transducer patch, comprising:
   a flexible printed circuit board; and
   a plurality of transducer clusters each of which comprises a plurality of dual-frequency transducers mounted to the flexible printed circuit board, wherein each of the dual-frequency transducers is operable to generate ultrasound having a low frequency ultrasound component and a high frequency ultrasound component, and wherein the dual-frequency transducers are arranged such that each of the transducer clusters has a width of about the wavelength of the low frequency ultrasound component.

14. The ultrasound transducer patch of claim 13, wherein each of the dual-frequency transducers has a unimorph structure.

15. The ultrasound transducer patch of claim 13, wherein each of the dual-frequency transducers has a bimorph structure.

16. The ultrasound transducer patch of claim 13, wherein the low frequency ultrasound component is generated at 50 kHz and the high frequency ultrasound component is generated at 3 MHz.

17. The ultrasound transducer patch of claim 13, wherein each of the transducer clusters includes 4 to 7 dual-frequency transducers.

18. The ultrasound transducer patch of claim 13, wherein the flexible printed circuit board includes a plurality of cut-out portions so as to be bendable about non-parallel axes.

19. The ultrasound transducer patch of claim 18, wherein the cut-out portions define multiple fingers, wherein each of the fingers includes first and second conductive tracks and at least one transducer cluster electrically connected to the conductive tracks, and wherein the conductive tracks are capable of supplying power to the dual-frequency transducers in the transducer cluster.

20. The ultrasound transducer patch of claim 18, wherein the cut-out portions define a mesh of lands interconnected by bridges, wherein each of the lands includes first and second conductive tracks and at least one transducer cluster electrically connected to the conductive tracks, and wherein the conductive tracks are capable of supplying power to the dual-frequency transducers in the transducer cluster.

21. A system for delivering ultrasound to a three dimensional target surface, comprising:
   an ultrasound transducer patch that conforms to the target surface, comprising (a) a flexible printed circuit board and (b) a plurality of transducer clusters each of which comprises a plurality of transducers mounted to the flexible printed circuit board, wherein each of the transducers is operable to generate ultrasound having a wavelength, and wherein the transducers are arranged such that each of the transducer clusters has a width of about the wavelength of the ultrasound; and
   an electrical driver operable to drive each of the transducers in each of the transducer clusters.

22. The system of claim 21, further comprising an electrical cable that couples the electrical driver to the ultrasound transducer patch.

23. The system of claim 21, wherein the electrical driver is incorporated into the ultrasound transducer patch.

24. The system of claim 21, wherein each of the transducers comprises a single-frequency transducer.

25. The system of claim 21, wherein each of the transducers comprises a dual-frequency transducer.

26. The system of claim 25, wherein each of the transducers has a unimorph structure.

27. The system of claim 25, wherein each of the transducers has a bimorph structure.

28. The system of claim 25, wherein the ultrasound generated by each of the transducers has a low frequency ultrasound component and a high frequency ultrasound component, and wherein the transducer cluster has a width of about the wavelength of the low frequency ultrasound component.

29. The system of claim 28, wherein the low frequency ultrasound component is generated at 50 kHz and the high frequency ultrasound component is generated at 3 MHz.

30. The system of claim 21, wherein each of the transducer clusters includes 4 to 7 transducers.

31. The system of claim 21, wherein the flexible printed circuit board includes a plurality of cut-out portions so as to be bendable about non-parallel axes.

32. The system of claim 31, wherein the cut-out portions define multiple fingers, wherein each of the fingers includes first and second conductive tracks and at least one transducer cluster electrically connected to the conductive tracks, and wherein the electrical driver is capable of supplying power to the transducers in the transducer cluster via the conductive tracks.

33. The system of claim 31, wherein the cut-out portions define a mesh of lands interconnected by bridges, wherein each of the lands includes first and second conductive tracks and at least one transducer cluster electrically connected to the conductive tracks, and wherein the electrical driver is capable of supplying power to the transducers in the transducer cluster via the conductive tracks.

34. The system of claim 21, wherein the transducer clusters are grouped into a plurality of sub-groups.

35. The system of claim 34, wherein the flexible printed circuit board includes first and second conductive tracks for each of the sub-groups, wherein the transducers in each sub-group are electrically connected to the conductive tracks, and wherein the electrical driver is capable of supplying power to the transducers in each sub-group via the conductive tracks so that the transducers in the sub-group are driven in parallel.

* * * * *